United States Patent
Nakamura et al.

(10) Patent No.: US 9,766,309 B2
(45) Date of Patent: Sep. 19, 2017

(54) MAGNETIC RESONANCE IMAGING APPARATUS AND APPARATUS FOR MEASURING RADIO FREQUENCY OUTPUT FOR THE SAME

(71) Applicant: TOSHIBA MEDICAL SYSTEMS CORPORATION, Otawara-Shi, Tochigi-Ken (JP)

(72) Inventors: Haruki Nakamura, Nasushiobara (JP); Kazuyuki Soejima, Nasushiobara (JP); Sojiyuuro Kato, Nasushiobara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 732 days.

(21) Appl. No.: 14/266,195

(22) Filed: Apr. 30, 2014

(65) Prior Publication Data

US 2014/0232407 A1    Aug. 21, 2014

Related U.S. Application Data

(63) Continuation of application No. PCT/JP2013/075717, filed on Sep. 24, 2013.

(30) Foreign Application Priority Data

Sep. 25, 2012 (JP) .................... 2012-211364

(51) Int. Cl.
G01V 3/00 (2006.01)
G01R 33/34 (2006.01)
(Continued)

(52) U.S. Cl.
CPC ...... *G01R 33/34092* (2013.01); *A61B 5/0037* (2013.01); *A61B 5/055* (2013.01);
(Continued)

(58) Field of Classification Search
CPC .......... G01R 33/34092; G01R 33/3607; G01R 33/3621; A61B 5/0037; A61B 5/055; A61B 5/7203
(Continued)

(56) References Cited

U.S. PATENT DOCUMENTS 5,172,059 A * 12/1992 den Boef ............. G01R 33/565
324/307
6,969,992 B2 * 11/2005 Vaughan ............ G01R 33/3415
324/309

(Continued)

FOREIGN PATENT DOCUMENTS

EP    1189071 A3 *  7/2004  ......... G01R 33/3628
JP    03051037 A  *  3/1991
(Continued)

OTHER PUBLICATIONS

International Search Report for PCT/JP2013/075717 mailed Oct. 22, 2013.
(Continued)

*Primary Examiner* — Susan Lee
(74) *Attorney, Agent, or Firm* — Nixon & Vanderhye P.C.

(57) ABSTRACT

An apparatus for measuring radio frequency output for a magnetic resonance imaging apparatus includes a plurality of directional couplers, a comparator, a switcher and a converter. The plurality of directional couplers are different in degree of coupling from each other, and attenuate an RF signal which is generated in an RF signal generator and amplified in an RF power amplifier. The comparator compares input-level information of a signal inputted into the RF power amplifier with a threshold value. The switcher switches to any one of the plurality of the directional couplers based on a result of the comparison so as to output an RF signal by the one directional coupler. The converter
(Continued)

performs a digital conversion of the RF signal from the one directional coupler so as to output a digital signal.

6 Claims, 10 Drawing Sheets

(51) Int. Cl.
    *A61B 5/055*     (2006.01)
    *G01R 33/36*     (2006.01)
    *A61B 5/00*     (2006.01)

(52) U.S. Cl.
    CPC ..... *G01R 33/3607* (2013.01); *G01R 33/3621* (2013.01); *A61B 5/7203* (2013.01)

(58) Field of Classification Search
    USPC .......................................................... 324/322
    See application file for complete search history.

(56) References Cited

U.S. PATENT DOCUMENTS

| | | | | |
|---|---|---|---|---|
| 7,075,366 B2 * | 7/2006 | Deem | ...................... | H03F 1/34 330/149 |
| 7,336,074 B2 * | 2/2008 | Yang | .................. | G01R 33/3415 324/309 |
| 7,615,999 B2 * | 11/2009 | Graesslin | ........... | G01R 33/3607 324/318 |
| 2014/0337397 A1 * | 11/2014 | Demharter | ................ | G06F 5/01 708/209 |

FOREIGN PATENT DOCUMENTS

| | | | |
|---|---|---|---|
| JP | 03051038 A | * | 3/1991 |
| JP | 5-45387 | | 2/1993 |
| JP | 5-87842 | | 4/1993 |
| JP | 7-246194 | | 9/1995 |
| JP | 9-19413 | | 1/1997 |
| JP | 11-253416 | | 9/1999 |

OTHER PUBLICATIONS

English Translation of International Preliminary Report on Patentability issued Mar. 31, 2015 for Application No. PCT/JP2013/075717.

* cited by examiner

| RF SIGNAL OUTPUTTED FROM RF POWER AMPLIFIER 63[W] | RF SIGNAL OUTPUTTED FROM DIRECTIONAL COUPLER 64[W] (1/10000) | CONVERTED RF SIGNAL AFTER OUTPUTTED FROM AD CONVERTER 66[W] (10000 TIMES) |
|---|---|---|
| 10000 | 1 | 10000 |
| 100 | 0.01 | 100 |

FIG. 3

| RF SIGNAL OUTPUTTED FROM RF POWER AMPLIFIER 43[W] | RF SIGNAL OUTPUTTED FROM DIRECTIONAL COUPLER 44a[W] (1/10000) | RF SIGNAL OUTPUTTED FROM DIRECTIONAL COUPLER 44b[W] (1/100) | CONVERTED RF SIGNAL AFTER OUTPUTTED FROM AD CONVERTER 48[W] |
|---|---|---|---|
| 10000 | 1 | 100 | 10000 |
| 100 | 0.01 | 1 | 100 |

: ADOPTION

| RF SIGNAL OUTPUTTED FROM RF POWER AMPLIFIER 43 [W] | RF SIGNAL OUTPUTTED FROM DIRECTIONAL COUPLER 44A [W] (VARIABILITY) | CONVERTED RF SIGNAL AFTER OUTPUTTED FROM AD CONVERTER 48 [W] |
|---|---|---|
| 10000 | 1 | 10000 |
| 100 | 1 | 100 |

FIG. 9

MAGNETIC RESONANCE IMAGING APPARATUS AND APPARATUS FOR MEASURING RADIO FREQUENCY OUTPUT FOR THE SAME

CROSS-REFERENCE TO RELATED APPLICATION

This application is a Continuation Application of No. PCT/JP2013/75717, filed on Sep. 24, 2013, and the PCT application is based upon and claims the benefit of priority from Japanese Patent Application No. 2012-211364, filed on Sep. 25, 2012, the entire contents of which are incorporated herein by reference.

FIELD

The present embodiments as an aspect of the present invention relate to a magnetic resonance imaging (MRI) apparatus and an apparatus for measuring radio frequency output for the same.

BACKGROUND

MRI is an imaging method for magnetically exciting nuclear spin of an object that is placed in a static magnetic field, with use of a radio frequency (RF) pulse having the Larmor frequency and reconstructing an image from nuclear magnetic resonance signals generated with the excitation. In MRI, an RF coil is used to transmit an RF pulse to an imaging region to excite nuclear magnetic resonance. The resonant frequency of the RF pulse is proportional to intensity of the static magnetic field of an MRI apparatus. For example, in the case of a static magnetic field of 1.5 tesla, the resonant frequency is 63.8 MHz.

In this frequency range, the RF pulse causes an increase in body temperature of the object. Accordingly, from the viewpoint of safety, an upper limit of the energy of the RF pulse transmitted to the object is prescribed by, for example, the International Electrotechnical Commission (IEC) standard or other standards. More specifically, energy of the RF pulse absorbed by 1 kg of living tissue is referred to as a specific absorption ratio (SAR). It is prescribed that SAR values for, for example, arbitrary 10 seconds and for 6 minutes do not exceed a first or second upper limit, respectively. The upper limit varies depending on whether the imaging region is the entire body or a partial region (such as the head).

In conventional technology, in order to satisfy the safety standards with respect to the SAR, an integrated value of the energy of an RF pulse transmitted to the object is calculated for each of preceding 1 second, 5 seconds, and 10 seconds. In any one of the following three cases, a pulse sequence is changed. A first case is that the integrated value exceeds a first predetermined value for the preceding one second. A second case is that the integrated value exceeds a second predetermined value for the preceding five seconds. A third case is that the integrated value exceeds a third predetermined value for the preceding 10 seconds. In some cases, the pulse sequence is changed by stopping operation of an RF pulse generator. However, this may cause interruption of imaging operation in the middle of the operation.

Accordingly, in the conventional technology, an SAR of the entire object and/or a partial imaging region is calculated at the time of pre-scan before imaging. If the calculated partial SAR exceeds the upper limit, an alarm is displayed and then the pulse sequence is changed so that the partial SAR does not exceed the upper limit. After it is verified that a dose to the object does not exceed the upper limit of the partial SAR, imaging is performed.

In order to calculate the SAR, there are conventional technologies which, at the time of a pre-scan before a main scan, measure an energy value (or energy control value) of an RF signal attenuated by one directional coupler with a fixed degree of coupling, the attenuated RF signal being based on an amplified RF signal from one RF power amplifier included in a transmitter. There are also conventional technologies which, at the time of the pre-scan before the main scan, measure an energy value of an RF signal attenuated by a plurality of directional couplers arranged in series on a transmission line, the attenuated RF signal being based on the amplified RF signal from the one RF power amplifier.

However, in the case of the conventional technologies involving one directional coupler with the fixed degree of coupling, the accuracy of an RF output monitor may deteriorate since MRI has a dynamic range with a wide transmission gain. While imaging of local regions, such as the limbs, requires about 100 to 200 [W], imaging of the entire body (such as imaging of an abdominal region) requires 10,000 to 20,000 [W] depending on the imaging sequence. The RF signal attenuated by the directional coupler is detected in a detector and is subjected to analog to digital (AD) conversion by an AD converter. Accordingly, in order to support a high power (10,000 to 20,000 [W]) signal, the degree of coupling of the directional coupler is set larger within a limit of a maximum input of the detector and the AD converter. In this case, a low-power signal (100 to 200 [W]) is excessively attenuated and its signal level becomes susceptible to noise floor and offset, which causes a problem of deteriorated accuracy in detection and A/D conversion.

In the case of the conventional technologies involving a plurality of the directional couplers, the influence of a reflective RF signal may be reduced. However, since the degree of coupling is invariable, the low-power signal (100 to 200 [W]) still suffers from the problem of deteriorated accuracy in detection and A/D conversion, as in the conventional technology involving one directional coupler.

BRIEF DESCRIPTION OF THE DRAWINGS

In accompanying drawings,

FIG. 3 is a table view showing contents of attenuation and correction of RF signals in the conventional MRI apparatus;

FIG. 9 is a table view showing contents of attenuation and correction of RF signals in the MRI apparatus according to the second embodiment.

DETAILED DESCRIPTION

Figure 1:
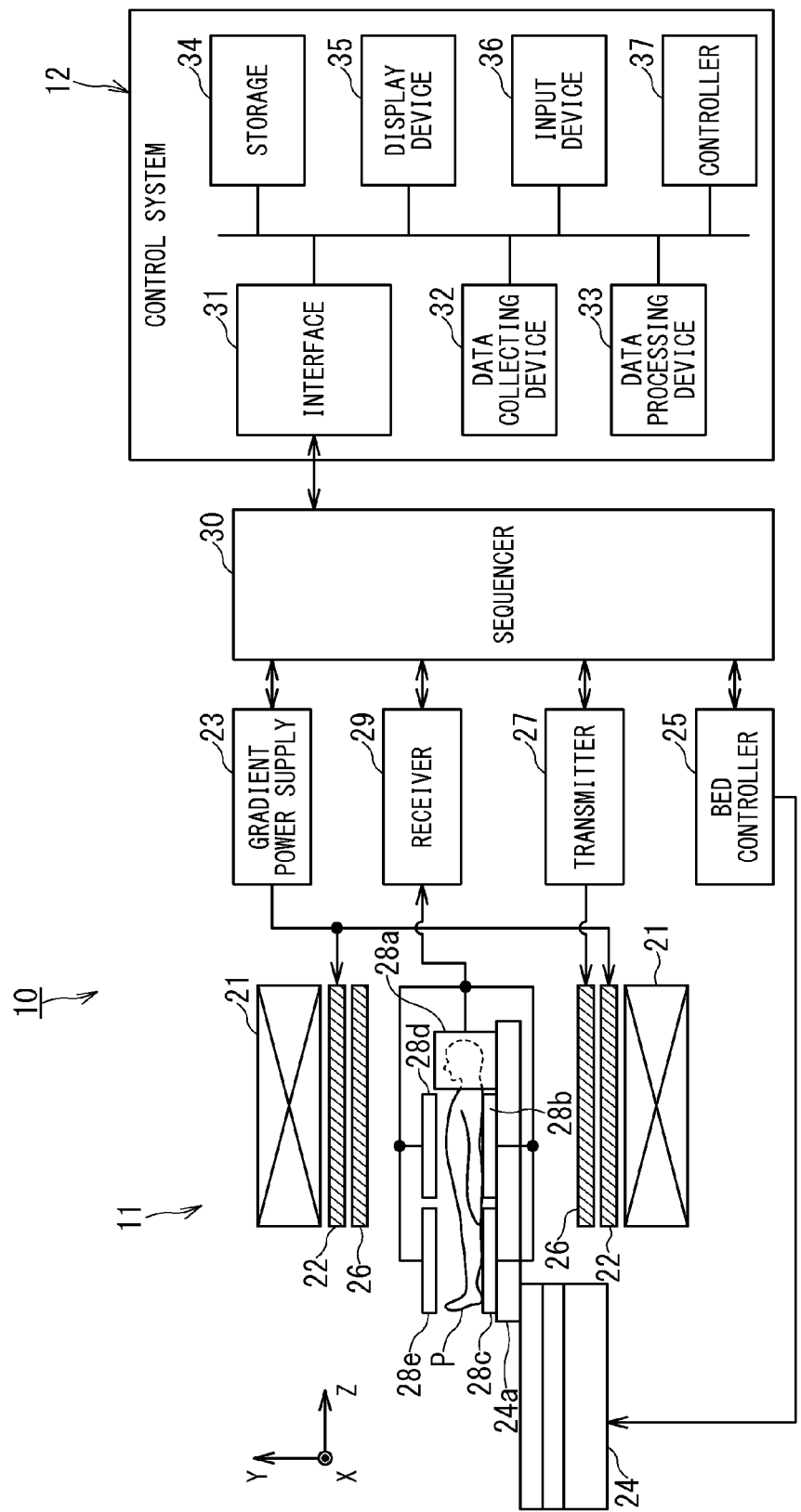
FIG. 1 is a schematic view showing a hardware configuration of an MRI apparatus according to a first embodiment.

A magnetic resonance imaging (MRI) apparatus and an apparatus for measuring radio frequency output for the MRI apparatus according to the present embodiments are described with reference to the accompanying drawings.

To solve the above-described problems, the present embodiments provide the apparatus for measuring radio frequency output for the MRI apparatus, including: a plurality of directional couplers different in degree of coupling from each other, and configured to attenuate a radio frequency signal which is generated in a radio frequency signal generator and amplified in a radio frequency power amplifier; a comparator configured to compare input-level information of a signal inputted into the radio frequency power amplifier with a threshold value; a switcher configured to switch to any one of the plurality of the directional couplers based on a result of the comparison so as to output a radio frequency signal by the one directional coupler; and a converter configured to perform a digital conversion of the radio frequency signal from the one directional coupler so as to output a digital signal.

To solve the above-described problems, the present embodiments provide the apparatus for measuring radio frequency output for the MRI apparatus, including: a directional coupler variable in degree of coupling, and configured to attenuate a radio frequency signal which is generated in a radio frequency signal generator and amplified in a radio frequency power amplifier; a signal controller configured to control the degree of coupling of the directional coupler; and a converter configured to perform a digital conversion of the radio frequency signal from the directional coupler so as to output a digital signal.

The apparatus for measuring RF output for the MRI apparatus according to the present embodiments is able to accurately measure an RF output with sufficient precision even when the RF output is small.

To solve the above-described problems, the present embodiments provide the MRI apparatus, including: a static magnetic field magnet configured to generate a static magnetic field; a gradient coil configured to generate a gradient magnetic field where intensity of a magnetic field varies, a transmission coil which is a radio frequency coil configured to generate a radio frequency magnetic field; a radio frequency power amplifier configured to amplify a radio frequency signal generated in a radio frequency signal generator and to provide the amplified radio frequency signal to the transmission coil; a plurality of directional couplers different in degree of coupling from each other, and configured to attenuate the radio frequency signal amplified in the radio frequency power amplifier; a comparator configured to compare input-level information of the signal inputted into the radio frequency power amplifier with a threshold value; a switcher configured to switch to any one of the plurality of the directional couplers based on a result of the comparison so as to output a radio frequency signal by the one directional coupler; a converter configured to perform a digital conversion of the radio frequency signal from the one directional coupler so as to output a digital signal; and a calculator configured to calculate a specific absorbed fraction based on the radio frequency signal outputted from the converter.

The MRI apparatus according to the present embodiments is able to accurately calculate an SAR with sufficient precision.

First Embodiment

FIG. 1 is a schematic view showing a hardware configuration of an MRI apparatus according to a first embodiment.

FIG. 1 illustrates an MRI apparatus 10 according to the first embodiment configured to image an object (patient) P. The MRI apparatus 10 is mainly made up of an imaging system 11 and a control system 12.

The imaging system 11 includes a static magnetic field magnet 21, a gradient coil 22, a gradient power supply 23, a bed 24, a bed controller 25, a transmission coil 26, a transmitter 27, reception coils 28a to 28e, a receiver 29, and a sequencer (sequence controller) 30.

The static magnetic field magnet 21 is formed into a hollow cylindrical shape on an outermost portion of a mount (not shown) so as to generate a uniform static magnetic field in an internal space. Examples of the static magnetic field magnet 21 include a permanent magnet and a superconducting magnet.

The gradient coil 22 is formed into a hollow cylindrical shape and is arranged inside the static magnetic field magnet 21. The gradient coil 22 is formed from a combination of an X-ch coil 22x, a Y-ch coil 22y, and a Z-ch coil 22z each corresponding to X, Y, and Z axes which are orthogonal to each other. These three coils, 22x, 22y, and 22z, individually receive current supply from the later-described gradient power supply 23 and generate gradient magnetic fields where the intensities of the magnetic fields vary along each of the X, Y, and Z axes. Note that a Z-axis direction is aligned with a direction of the static magnetic field.

The gradient magnetic fields in each of the X, Y, and Z axes generated by the gradient coil 22 correspond to, for example, a gradient magnetic field Gr for readout, a gradient magnetic field Ge for phase encoding, and a gradient magnetic field Gs for slice selection, respectively. The gradient magnetic field Gr for readout is used to change a frequency of a nuclear magnetic resonance (NMR) signal in accordance with a spatial location. The gradient magnetic field Ge for phase encoding is used to change a phase of an NMR signal in accordance with the spatial location. The gradient magnetic field Gs for slice selection is used to arbitrarily determine an imaging cross section.

The gradient power supply 23 supplies current to the gradient coil 22 based on pulse sequence execution data sent from the sequencer 30.

The bed 24 includes a top plate 24a to lay the object P thereon. Under control of the later-described bed controller 25, the top plate 24a of the bed 24 is inserted into a hollow (imaging port) of the gradient coil 22 with the object P being laid thereon. The bed 24 is generally placed so that its longitudinal direction is parallel to a central axis of the static magnetic field magnet 21.

The bed controller 25 drives, under control of the sequencer 30, the bed 24 so as to move the top plate 24a in a longitudinal direction and in a vertical direction.

The transmission coil 26 is arranged inside the gradient coil 22 to generate a radio frequency (RF) magnetic field upon reception of an RF pulse from the transmitter 27.

The transmitter 27 transmits an RF pulse corresponding to the Larmor frequency to the transmission coil 26 based on the pulse sequence execution data sent from the sequencer 30. The configuration of the transmitter 27 is described later.

The reception coils 28a to 28e are arranged inside the gradient coil 22 to receive an NMR signal emitted from the object P due to the influence of the RF magnetic field. The reception coils 28a to 28e are array coils having a plurality of element coils which respectively receive magnetic resonance signals emitted from the object P. Upon reception of the NMR signals with the respective element coils, the received NMR signals are outputted to the receiver 29.

The reception coil 28a is a head-portion coil mounted on the head of the object P. The reception coils 28b and 28c are backbone coils arranged between the back of the object P and the top plate 24a. The reception coils 28d and 28e are abdominal-portion coils each mounted on the abdominal side of the object P. The MRI apparatus 10 may include a coil for use in both transmission and reception.

The receiver 29 generates NMR signal data based on NMR signals which are outputted from the reception coils 28a to 28e based on the pulse sequence execution data sent from the sequencer 30. Upon generation of the NMR signal data, the receiver 29 transmits the NMR signal data to the control system 12 via the sequencer 30.

The receiver 29 has a plurality of receiving channels configured to receive the NMR signals outputted from the plurality of the element coils included in the reception coils 28a to 28e. When an element coil to be used for imaging is notified from the control system 12, the receiver 29 allocates a receiving channel to the notified element coil so as to receive an NMR signal outputted from the notified element coil.

The sequencer 30 is connected to the gradient power supply 23, the bed controller 25, the transmitter 27, the receiver 29, and the control system 12. The sequencer 30 includes unshown processors such as a central processing unit (CPU) and a memory. The sequencer 30 stores sequence information describing control information necessary for driving the gradient power supply 23, the bed controller 25, the transmitter 27, and the receiver 29. The control information is, for example, motion control information such as intensity, application time, and application timing of pulse current that should be applied to the gradient power supply 23.

The sequencer 30 also drives the bed controller 25 in accordance with the stored specified sequence so as to move the top plate 24a back and forth with respect to the mount in a Z direction. The sequencer 30 further drives the gradient power supply 23, the transmitter 27, and the receiver 29 in accordance with the stored specified sequence so as to generate an X axis-gradient magnetic field Gx, a Y axis-gradient magnetic field Gy, a Z axis-gradient magnetic field Gz, and an RF signal inside the mount.

The control system 12 performs control of an entire MRI apparatus 10, data collection, image reconstruction, and the like. The control system 12 has an interface 31, a data collecting device 32, a data processing device 33, a storage 34, a display device 35, an input device 36, and a controller 37.

The interface 31 is connected to the gradient power supply 23, the bed controller 25, the transmitter 27, and the receiver 29 of the imaging system 11 via the sequencer 30. The interface 31 controls input/output of the signals delivered and received between each of these connected units and the control system 12.

The data collecting device 32 collects NMR signal data transmitted from the receiver 29 via the interface 31. Once the NMR signal data is collected, the data collecting device 32 stores the collected NMR signal data in the storage 34.

The data processing device 33 performs post-processing, i.e., reconfiguration processing such as Fourier transform, on the NMR signal data stored in the storage 34 so as to generate spectrum data or image data of desired nuclear spin in the object P. In the case of imaging a positioning image, the data processing device 33 generates, based on the NMR signals received in each of the plurality of the element coils included in the reception coils 28a to 28e, profile data indicating NMR signal distribution in an array direction of the element coils, for each of the element coils. The data processing device 33 stores the generated various data in the storage 34.

The storage 34 stores the NMR signal data collected in the data collecting device 32 and the image data generated in the data processing device 33 for each object P.

The display device 35 displays various kinds of information, including the spectrum data or image data generated in the data processing device 33. Examples of the display device 35 include a display device, such as liquid crystal displays.

The input device 36 receives various operations and information inputs from an operator. As the input device 36, a pointing device such as a mouse and a trackball, a selector device such as a mode selector switch, or an input device such as a keyboard, can suitably be used.

The controller 37, having an unshown central processing unit (CPU), a memory and the like, controls each of the units described in the foregoing for comprehensive control of the MRI apparatus 10.

Figure 2:
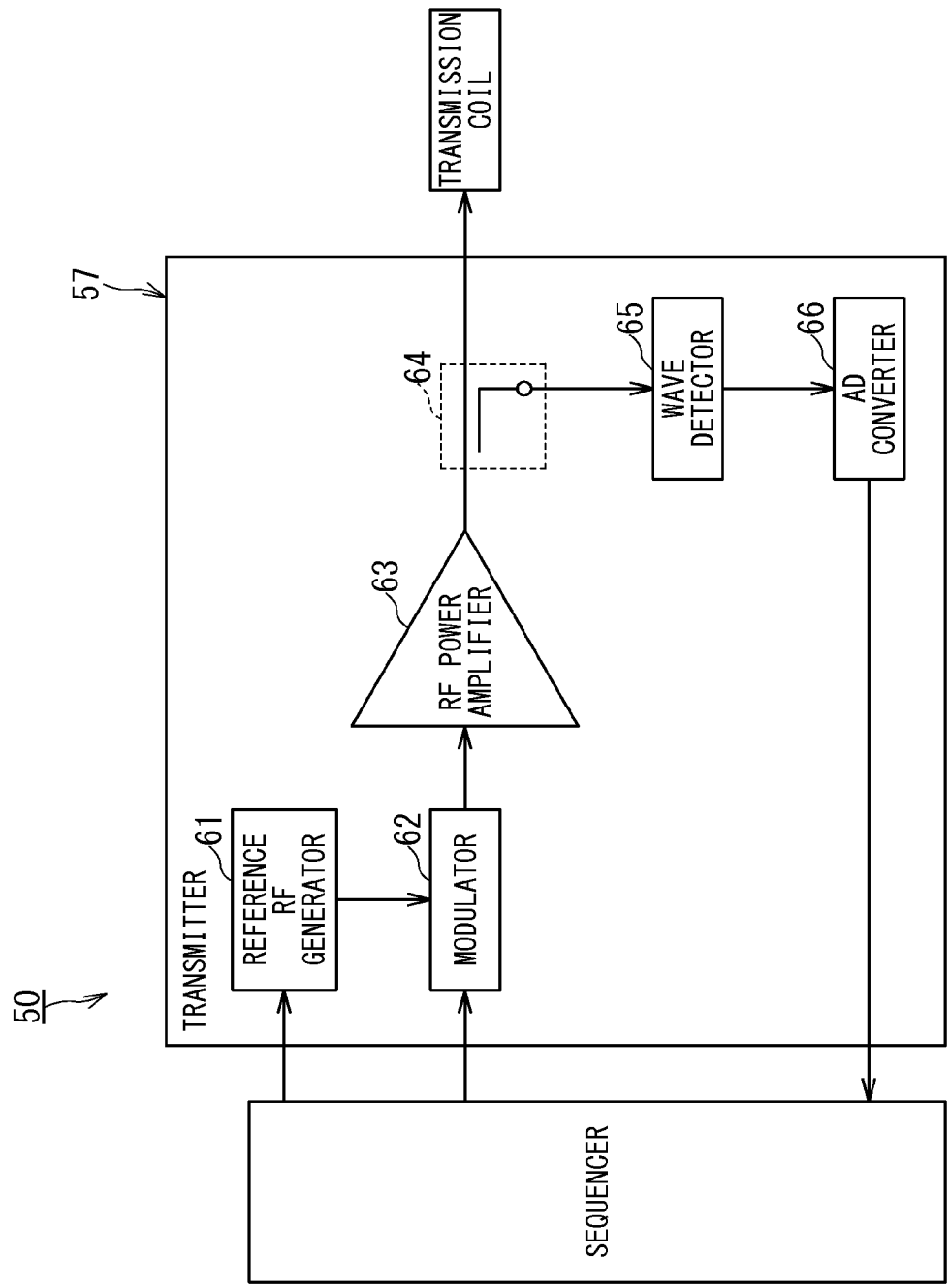
FIG. 2 is a diagram showing a configuration of a transmitter in a conventional MRI apparatus.

FIG. 2 is a diagram showing a configuration of a transmitter in a conventional MRI apparatus.

A transmitter 57 in a conventional MRI apparatus 50 includes a reference RF generator 61, a modulator 62, an RF power amplifier 63, a directional coupler 64, a wave detector 65, and an analog to digital (AD) converter 66.

The reference RF generator 61 generates a reference RF signal (RF carrier wave) under the control of the sequencer.

The modulator 62 modulates, under the control of the sequencer, the reference RF signal generated in the reference RF generator 61 into an RF signal with a specified waveform.

The RF power amplifier 63 amplifies the RF signal modulated in the modulator 62 and provides it to the transmission coil via the directional coupler 64. The amplified RF signal is transferred to the transmission coil, and RF is emitted from the transmission coil to the object. The transmission coil includes a transmission coil for whole body and a transmission coil for local region.

The directional coupler 64 is arranged on a transmission line of the RF signal in non-contact with the transmission line. The directional coupler 64 is configured to attenuate the RF signal, which is transferred to the transmission coil, with a required degree of coupling (coupling coefficient) and to send it to the wave detector 65. The directional coupler 64 is a radio frequency device for attenuating the output (RF power) of the RF signal (a traveling wave and a reflected wave). The output signal of the directional coupler 64 is detected by the wave detector 65 in an MR signal processing substrate and is digital-converted by the AD converter 66. The output data of the AD converter 66 is used in order to calculate an SAR.

FIG. 3 is a table view showing contents of attenuation and correction of the RF signals in the conventional MRI apparatus.

A large degree of coupling is set for the directional coupler 64 within a limit of a maximum input of the wave detector 65 and/or the AD converter 66 so that high-power (10,000 to 20,000 [W]) signals may be supported. For example, consider the case where the degree of coupling of the directional coupler 64 is 1/10,000. When a high-power (10,000 [W]) RF signal is outputted from the RF power amplifier 63, a signal of 1 [W] is inputted into the wave detector 65 via the directional coupler 64.

When a low-power (100 [W]) RF signal is outputted from the RF power amplifier 63, a signal of 0.01 [W] is inputted into the wave detector 65 via the directional coupler 64.

The signals which are digital-processed by the AD converter 66 are outputted to the sequencer, and the high-power and low-power RF signals are respectively converted to 10,000 [W] and 100 [W] based on a 1/10,000 degree of coupling of the directional coupler 64.

Since the degree of coupling of the directional coupler 64 is adjusted based on the high-power signal, the low-power signal is excessively attenuated and an output of the low-power signal from the directional coupler 64 becomes as small as 0.01 [W]. Therefore, the signal level of the low-power signal is susceptible to the influence of noise floor and offset, which causes the problem of deteriorated accuracy in detection and A/D conversion.

Figure 4:
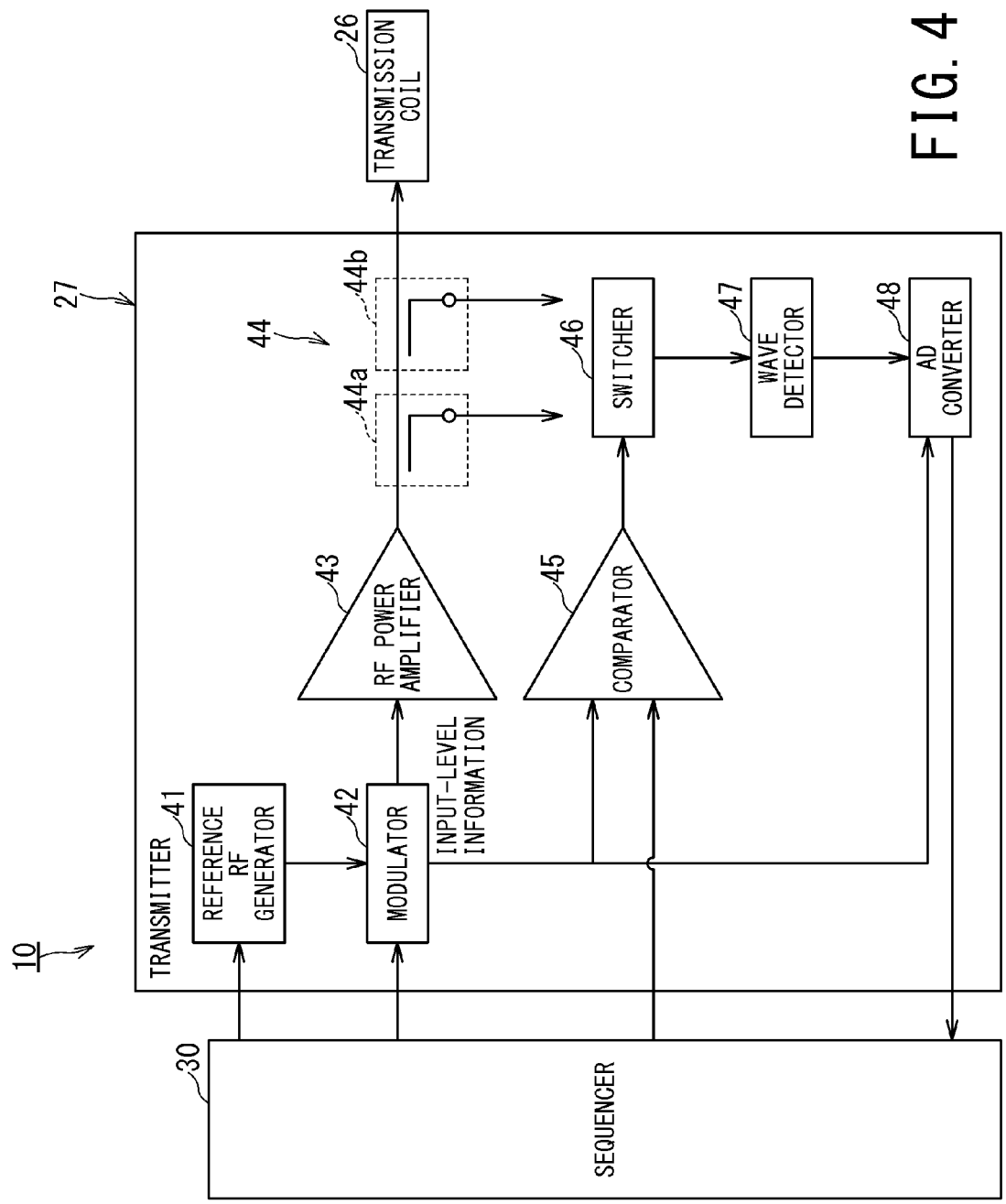
FIG. 4 is a diagram showing a configuration of a transmitter in the MRI apparatus according to the first embodiment.

FIG. 4 is a diagram showing a configuration of the transmitter 27 in the MRI apparatus 10 according to the first embodiment.

The transmitter 27 in the MRI apparatus 10 according to the first embodiment includes a reference RF generator 41, a modulator 42, an RF power amplifier 43, a directional coupler unit 44, a comparator 45, a switcher 46, a wave detector 47, and an AD converter 48. The directional coupler unit 44, the comparator 45, the switcher 46, the wave detector 47, and the AD converter 48 constitute an apparatus for measuring RF output in this embodiment.

The reference RF generator 41 generates a reference RF signal (RF carrier wave) under the control of the sequencer 30.

The modulator 42 modulates, under the control of the sequencer 30, the reference RF signal generated in the reference RF generator 41 into an RF signal with a specified waveform.

The RF power amplifier 43 amplifies the RF signal modulated in the modulator 42 and provides it to the transmission coil 26 via the directional coupler unit 44. The amplified RF signal is transferred to the transmission coil 26, and RF is emitted from the transmission coil 26 to the object. The transmission coil 26 includes a transmission coil for whole body and a transmission coil for local region.

The directional coupler unit 44 includes a plurality of directional couplers 44a, 44b, . . . different in degree of coupling from each other. A description is hereinafter given of the directional coupler unit 44 including two directional couplers 44a and 44b. The directional couplers 44a and 44b are arranged on a transmission line of the RF signal in series in non-contact with the transmission line. The directional couplers 44a and 44b are configured to attenuate RF signals, which are transferred to the transmission coil 26, with different degrees of coupling, and to send attenuated the signals to the switcher 46.

A signal is inputted from the modulator 42 to the RF power amplifier 43. The comparator 45 compares the input-level information (gain information) of the signal with a threshold value that is a reference sent from the sequencer 30. Based on the comparison output, the comparator 45 controls the switcher 46. The comparator 45 controls the switcher 46 which switches to any of the directional couplers 44a and 44b. The output signal of the comparator 45 is used as a control signal of the switcher 46.

The RF signals obtained by attenuating RF signals in the directional couplers 44a and 44b are inputted into the switcher 46. The switcher 46 switches to any one of the directional couplers 44a and 44b in response to the control signal of the comparator 45 so as to output an RF signal from the one directional coupler 44a or 44b to the wave detector 47. The output signal of the switcher 46 is detected by the wave detector 47 in an MR signal processing substrate and is digital-converted by the AD converter 48. In digital conversion of the output signal of the wave detector 47, the AD converter 48 multiplies the output signal by a correction coefficient corresponding to the input-level information of the signal inputted into the RF power amplifier 43 from the modulator 42. The output data of the AD converter 48 is transmitted to the control system 12 (shown in FIG. 1) via the sequencer 30, and the control system 12 uses the data to calculate an SAR.

Figure 5:
FIG. 5 is a table view showing contents of attenuation and correction of RF signals in the MRI apparatus according to the first embodiment.

FIG. 5 is a table view showing contents of attenuation and correction of the RF signals in the MRI apparatus 10 according to the first embodiment.

A degree of coupling is set for the directional couplers 44a and 44b within a limit of a maximum input of the wave detector 47 and/or the AD converter 48 so that high-power (10,000 to 20,000 [W]) signals may be supported. For example, consider the case where the degree of coupling of the directional coupler 44a is 1/10,000 and the degree of coupling of the directional coupler 44b is 1/100. When a high-power (10,000 [W]) RF signal is outputted from the RF power amplifier 43, a signal of 1 [W] is inputted into the switcher 46 via the directional coupler 44a, and a signal of 100 [W] is inputted into the switcher 46 via the directional coupler 44b.

When a low-power (100 [W]) RF signal is outputted from the RF power amplifier 43, a signal of 0.01 [W] is inputted into the switcher 46 via the directional coupler 44a, and a signal of 1 [W] is inputted into the switcher 46 via the directional coupler 44b.

When the RF signal of 10,000 [W] is outputted from the RF power amplifiers 43, the switcher 46 adopts and outputs the signal of 1 [W] which is outputted from the directional coupler 44a. When the RF signal of 100 [W] is outputted from the RF power amplifier 43, the switcher 46 adopts and outputs the signal of 1 [W] which is outputted from the directional coupler 44b.

The AD converter 48 converts an output value based on the degree of coupling that is a correction coefficient corresponding to the input-level information from the modulator 42. More specifically, when the output signal of the directional coupler 44a is adopted, the AD converter 48 multiplies the output signal of the directional coupler 44a by 10,000 so as to convert the output signal into an output equivalent to 10,000 [W]. When the output signal of the directional coupler 44b is adopted, the AD converter 48 multiplies the output signal of the directional coupler 44b by 100 so as to convert the output signal into an output equivalent to 100 [W].

According to the aforementioned examples of the degree of coupling of the directional couplers 44a and 44b and/or the output of the RF signals, the output of the switcher 46 results to be 1 [W] in both the cases of the high-power signal and the low-power signal. Therefore, the signal level of both the high-power signal and the low-power signal is less susceptible to the influence of noise floor and offset, so that accuracy in detection and A/D conversion is enhanced. It should naturally be understood that the plurality of the directional couplers 44a and 44b different in degree of coupling from each other may also enhance the accuracy in detection and A/D conversion in cases other than those described in the foregoing.

Next, the control system 12 shown in FIG. 1 controls the entire MRI apparatus 10 based on operation from an operator, while converting raw data transmitted from the sequencer 30 into k space data and reconstructing an image based on the k space data. The control system 12 also calculates an SAR of the entire object P and/or a partial imaging region at the time of a pre-scan before a main scan (imaging). If the calculated partial SAR exceeds the upper limit, an alarm is displayed and then the pulse sequence is changed so that the partial SAR does not exceed the upper limit. After it is verified that the dose to the object does not exceed the upper limit of the partial SAR, the main scan is performed. The pre-scan is a scan performed before the main scan, and its purpose includes at least adjustment of a transmission gain.

There has been described the process at the time of pre-scan in the MRI apparatus 10 according to the first embodiment. However, the above-described process at the time of pre-scan is also applicable to the process at the time of main scan. Now, the process of the main scan is described with reference to FIG. 4.

When an RF signal is transmitted from the transmission coil 26 to nuclear spin which is in a thermal equilibrium state due to the static magnetic field, the nuclear spin can be inclined (excited) by a certain angle. This angle is referred to as a "flip angle." First, in the pre-scan performed before the main scan, an RF level, i.e., an RF signal output in the case of an excitation pulse having a reference flip angle (for example, 90 degrees) is measured. In general, the RF level varies depending on load conditions of the transmission coil 26. For example, the measured RF value varies depending on the object P (depending on the body thickness), and/or depending on positional relationship between the transmission coil 26 and the object P (depending on the imaging regions) even when the object P is the same.

Next, based on the RF level, an RF signal output is set for each RF pulse (including a pre-pulse and an excitation pulsed) included in a pulse sequence. The input-level information of a signal inputted into the RF power amplifier 43 is controlled by automatic power control (APC) so that the set RF signal output is obtained. Typical pre-pulse examples include fat suppressor pulses such as a short TI inversion recovery (STIR) pulse, a chemical shift selective (CHESS) pulse, a spectral presaturation with inversion recovery (SPIR) pulse, and a spectral attenuated inversion recovery (SPAIR) pulse. The excitation pulse is a pulse for inclining the nuclear spin by a flip angle.

As described in the foregoing, the RF signal output is set based on the RF level for each RF pulse included in the pulse sequence. Based on this RF signal output, the input-level information of a signal inputted into the RF power amplifier 43 in the main scan can be predicted for each RF pulse.

Figure 6:
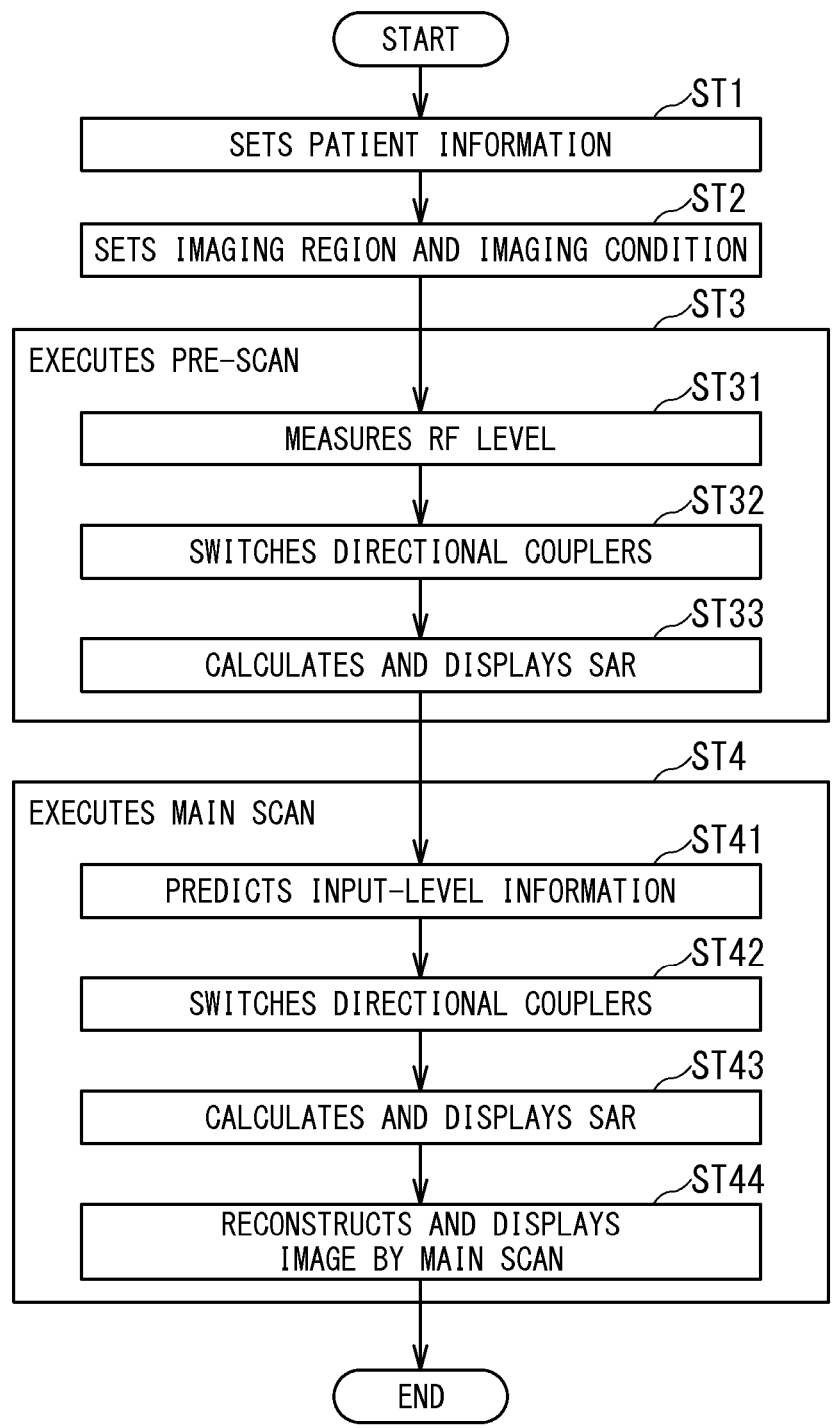
FIG. 6 is a flow chart showing an operation of the MRI apparatus according to the first embodiment.

A description is now given of the operation of the MRI apparatus 10 according to the first embodiment with reference to FIGS. 4 and 6.

FIG. 6 is a flow chart showing an operation of the MRI apparatus 10 according to the first embodiment.

The MRI apparatus 10 sets patient information on the object P (such as weight and height) based on the information inputted by an operator on an imaging condition edit screen with the input device (shown in FIG. 1) (step ST1).

Based on the information inputted by the operator on the imaging condition edit screen with the input device 36 (shown in FIG. 1), the MRI apparatus 10 sets an imaging region and imaging conditions (step ST2). The imaging conditions include a type of the pulse sequence (including the number of RF pulses), the number of multi-slices, and a slice thickness.

Next, the MRI apparatus 10 executes a pre-scan of the object P (step ST3). In the pre-scan in step ST3, the MRI apparatus 10 measures an RF level, i.e., an RF signal output in the case of the excitation pulse with a reference flip angle (for example, 90 degrees), based on the imaging region set in step ST2 (step ST31). In the pre-scan in step ST3, the MRI apparatus 10 compares the input-level information of a signal inputted into the RF power amplifier 43 at the time of measurement in step ST31 with a threshold value. Accordingly, the directional couplers 44a and 44b configured to attenuate the RF signal transferred to the transmission coil 26 are switched (step ST32). The RF level varies depending on the object P and the imaging region.

In step ST3, the MRI apparatus 10 detects an RF signal attenuated by the directional coupler 44a or 44b, and multiplies the RF signal by a correction coefficient corresponding to the input-level information of the signal inputted into the RF power amplifier 43 so as to produce digital data. Based on the digital data, the MRI apparatus 10 calculates SARs (entire SAR, partial SAR) and displays them on the display device 35 (shown in FIG. 1) (step ST33).

Next, the MRI apparatus 10 transmits sequence information in conformity with the imaging conditions set in step ST2 for the sequencer 30 to execute a main scan of the object P (step ST4). In step ST4, the MRI apparatus 10 sets an RF signal output based on the RF level measured in step ST31 for each RF pulse (including a pre-pulse and an excitation pulse) included in the pulse sequence in conformity with the imaging conditions set in step ST2. Based on the RF signal output, the input-level information of a signal inputted into the RF power amplifier 43 in the main scan is predicted for each RF pulse (step ST41). In step ST4, the MRI apparatus 10 compares the input-level information predicted in step ST41 with the threshold value so as to switch between the directional couplers 44a and 44b which are configured to attenuate the RF signal transferred to the transmission coil 26 (step ST42).

In step ST4, the MRI apparatus 10 detects an RF signal attenuated by the directional coupler 44a or 44b, and multiplies the RF signal by a correction coefficient corresponding to the input-level information of the signal inputted into the RF power amplifier 43 to produce digital data. Based on the digital data, the MRI apparatus 10 calculates SARs (entire SAR, partial SAR) and displays them on the display device 35 (shown in FIG. 1) (step ST43). In step ST4, the MRI apparatus 10 also reconstructs an image (a two-dimensional image, a three-dimensional image) based on raw data collected in the main scan and displays the image on the display device 35 (shown in FIG. 1) (step ST44). In step ST44, the SARs during main scan are monitored.

According to the transmitter 27 in the MRI apparatus 10 according to the first embodiment, the intensity of the RF signal to be detected and A/D-converted at the time of pre-scan and main scan is controlled. As a result, even when an RF output is small, the RF output can accurately be measured with sufficient precision. Therefore, the MRI apparatus 10 according to the first embodiment is able to accurately calculate the SAR with sufficient precision.

Second Embodiment

Figure 7:
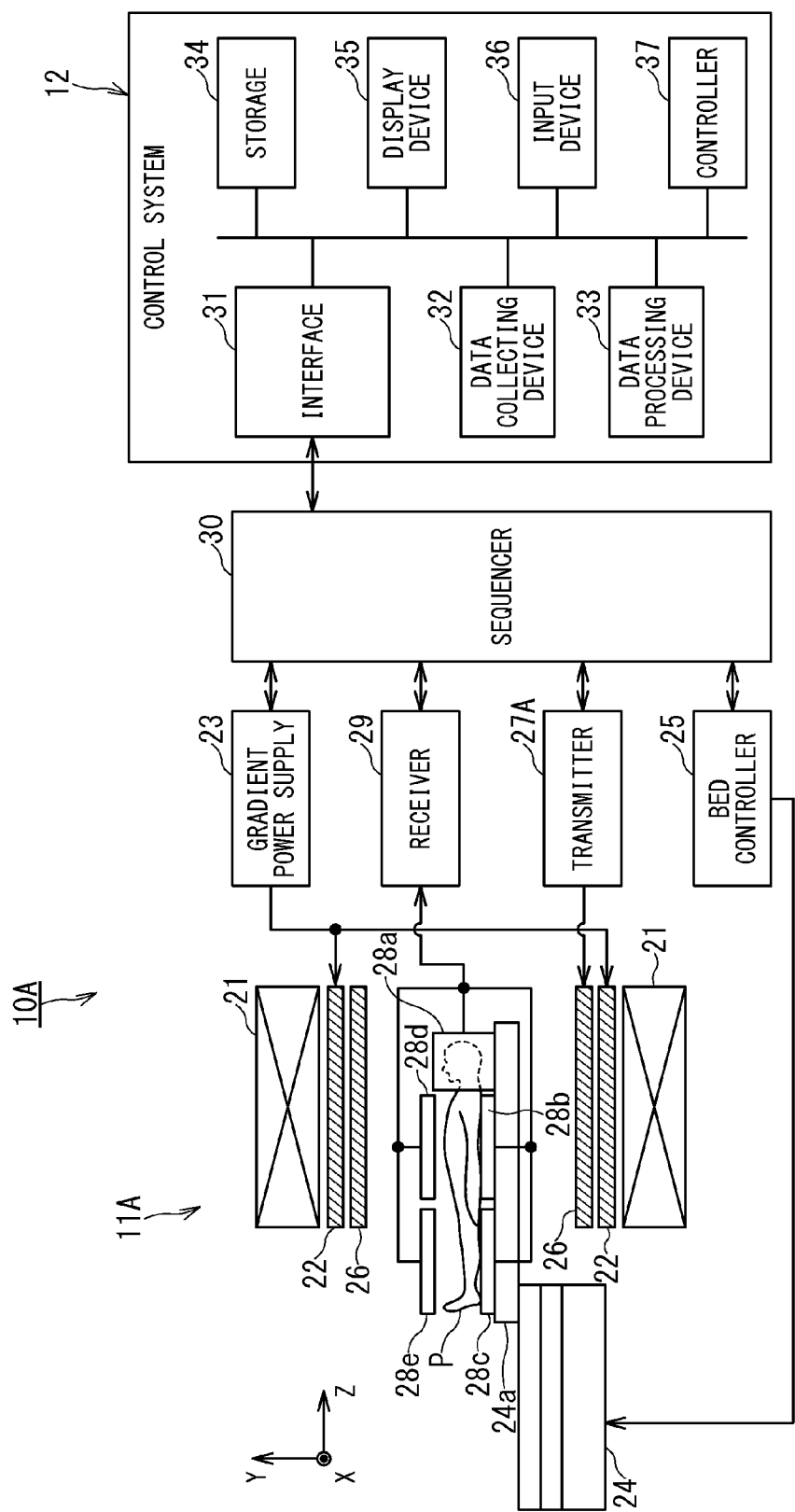
FIG. 7 is a schematic view showing a hardware configuration of an MRI apparatus according to a second embodiment.

FIG. 7 is a schematic view showing a hardware configuration of an MRI apparatus according to a second embodiment.

FIG. 7 illustrates an MRI apparatus 10A according to the second embodiment configured to image an object (patient) P. The MRI apparatus 10A is mainly made up of an imaging system 11A and a control system 12.

The imaging system 11A includes a static magnetic field magnet 21, a gradient coil 22, a gradient power supply 23, a bed 24, a bed controller 25, a transmission coil 26, a transmitter 27A, reception coils 28a to 28e, a receiver 29, and a sequencer 30.

Component members of the MRI apparatus 10A according to the second embodiment shown in FIG. 7 which are identical to those of the MRI apparatus 10 according to the first embodiment shown in FIG. 1 are designated by identical reference numerals to omit description.

Like the transmitter 27 shown in FIG. 1, the transmitter 27A transmits an RF pulse corresponding to the Larmor frequency to the transmission coil 26 based on pulse sequence execution data sent from the sequencer 30.

Figure 8:
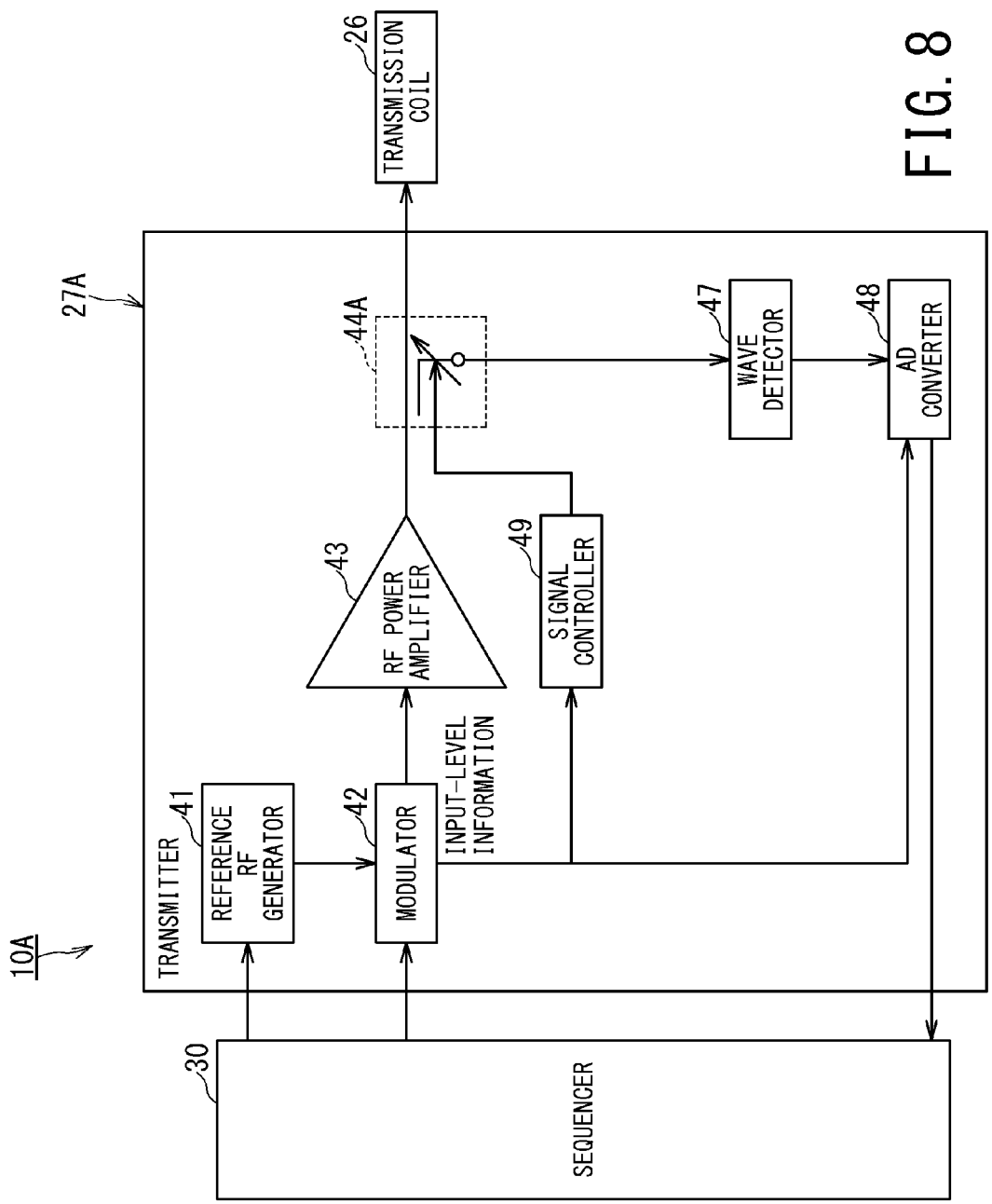
FIG. 8 is a diagram showing a configuration of a transmitter in the MRI apparatus according to the second embodiment.

FIG. 8 is a diagram showing a configuration of the transmitter 27A in the MRI apparatus 10A according to the second embodiment.

The transmitter 27A in the MRI apparatus 10A according to the second embodiment includes a reference RF generator 41, a modulator 42, an RF power amplifier 43, a directional coupler 44A variable in degree of coupling, a wave detector 47, an AD converter 48, and a signal controller 49. The directional coupler 44A variable in degree of coupling, the wave detector 47, the AD converter 48, and the signal controller 49 constitute an apparatus for measuring RF output of this embodiment.

Component members of the transmitter 27A shown in FIG. 8 which are identical to those of the transmitter 27 shown in FIG. 4 are designated by identical reference numerals to omit description.

When one directional coupler 44A variable in degree of coupling is provided, the switcher 46 (shown in FIG. 4) becomes unnecessary, and the RF signal attenuated by the directional coupler 44A is directly outputted to the wave detector 47.

The directional coupler 44A is arranged on a transmission line of the RF signal in non-contact with the transmission line. The directional coupler 44A is configured to attenuate the RF signal, which is transferred to the transmission coil 26, with a variable degree of coupling and to send it to the wave detector 47. The directional coupler 44A is a radio frequency device for attenuating the electric power of the RF signal. The output signal of the directional coupler 44 is detected by the wave detector 47 in an MR signal processing substrate and is digital-converted by the AD converter 48. In digital conversion of the output signal of the wave detector 47, the AD converter 48 multiplies the output signal by a correction coefficient corresponding to the input-level information of the signal inputted from the modulator 42 to the RF power amplifier 43 to produce data. The output data of the AD converter 48 is transmitted to the control system 12 (shown in FIG. 7) via the sequencer 30, and the control system 12 uses the data to calculate an SAR.

To control change in degree of coupling of the directional coupler 44A, the input-level information of the signal inputted from the modulator 42 to the RF power amplifier 43 is inputted into the signal controller 49. The signal controller 49 changes the degree of coupling of the directional coupler 44A based on the input-level information.

FIG. 9 is a table view showing contents of attenuation and correction of the RF signals in the MRI apparatus 10A according to the second embodiment.

An upper limit of the degree of coupling of the directional couplers 44A variable in degree of coupling is set within a limit of a maximum input of the wave detector 47 and/or the AD converter 48 so that high-power (10,000 to 20,000 [W]) signals may be supported. For example, consider the case where the degree of coupling of the directional coupler 44A variable in degree of coupling can be changed to 1/10,000. When a high-power (10,000 [W]) RF signal is outputted from the RF power amplifier 43, a signal of 1 [W] is inputted into the wave detector 47 via the directional coupler 44A.

A lower limit of the degree of coupling of the directional coupler 44A variable in degree of coupling is also set so that low-power (100 [W]) signals may be supported. For example, consider the case where the degree of coupling of the directional coupler 44A variable in degree of coupling can be changed to 1/100. When a low-power (100 [W]) RF signal is outputted from the RF power amplifier 43, a signal of 1 [W] is inputted into the wave detector 47 via the directional coupler 44A.

The AD converter 48 converts the output value based on the degree of coupling that is a correction coefficient corresponding to the input-level information from the modulator 42. More specifically, when the degree of coupling is 1/10,000, the AD converter 48 multiplies the output signal of the directional coupler 44A by 10,000 so as to convert the output signal into an output equivalent to 10,000 [W]. When the degree of coupling is 1/100, the AD converter 48 multiplies the output signal of the directional coupler 44A by 100 so as to convert the output signal into an output equivalent to 100 [W].

According to the aforementioned examples of the degree of coupling of the directional coupler 44A and/or the output of the RF signals, the output of the directional coupler 44A results to be 1 [W] in both the cases of the high-power signal and the low-power signal. Therefore, the signal level of both the high-power signal and the low-power signal is less susceptible to the influence of noise floor and offset, so that accuracy in detection and A/D conversion is enhanced. It should naturally be understood that the directional coupler 44A variable in degree of coupling may also enhance the accuracy in detection and A/D conversion in cases other than the above-described example.

Next, the control system 12 shown in FIG. 7 calculates SARs of the entire object P and/or a partial imaging region at the time of pre-scan before imaging. If the calculated partial SAR exceeds the upper limit, an alarm is displayed and then the pulse sequence is changed so that the partial SAR does not exceed the upper limit. After it is verified that the dose to the object P does not exceed the upper limit of the partial SAR, the main scan is performed.

There has been described the process at the time of pre-scan in the MRI apparatus 10A according to the second embodiment. However, the aforementioned process at the time of pre-scan is also applicable to the process at the time of main scan, as described in the MRI apparatus 10 according to the first embodiment.

Figure 10:
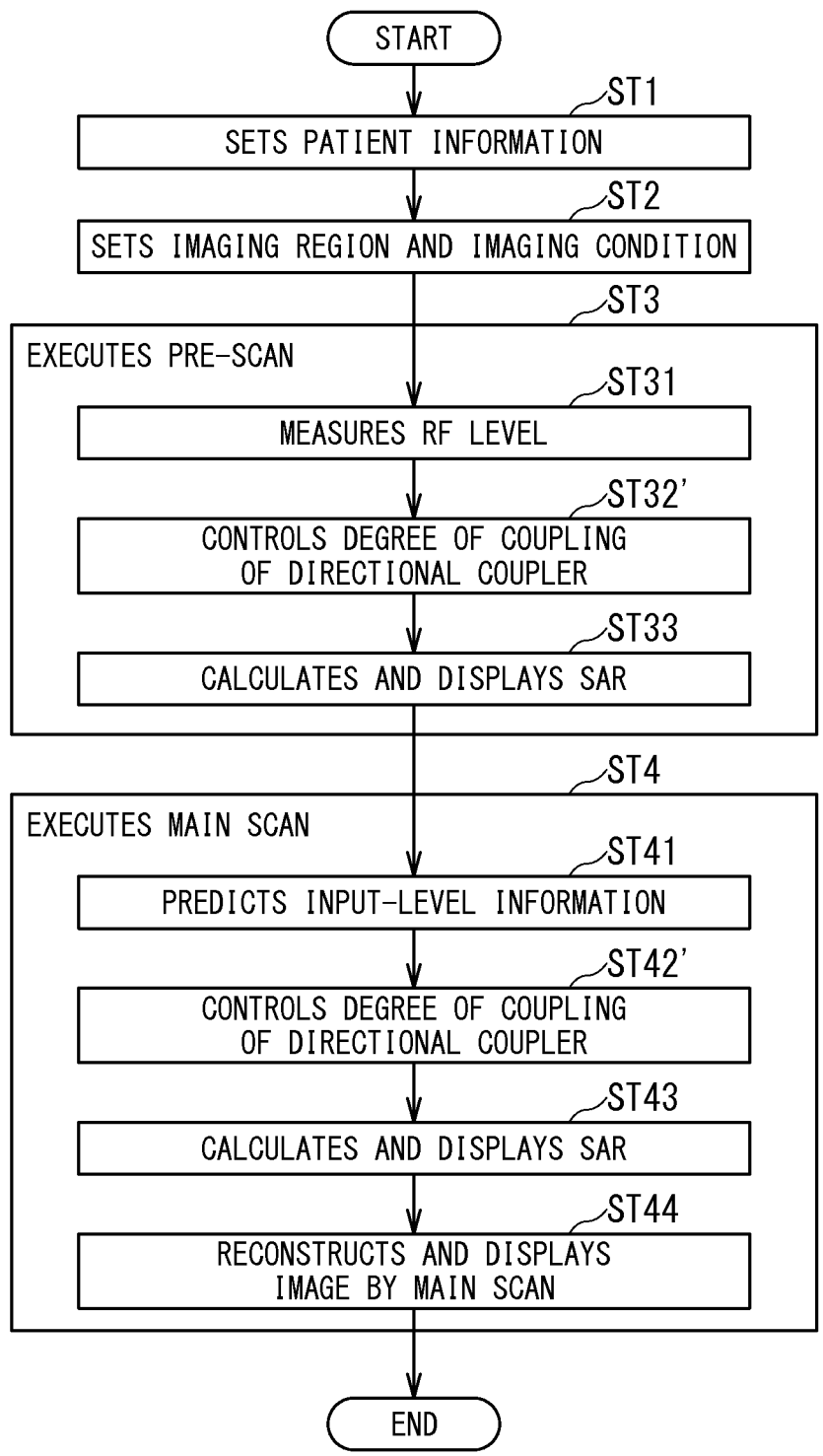
FIG. 10 is a flow chart showing an operation of the MRI apparatus according to the second embodiment.

A description is now given of the operation of the MRI apparatus 10A according to the second embodiment with reference to FIGS. 8 and 10.

FIG. 10 is a flow chart showing an operation of the MRI apparatus 10A according to the second embodiment.

In the flow chart of FIG. 10, the steps identical to those in the flow chart of FIG. 6 are designated by identical step numbers to omit description.

In the pre-scan in step ST3, the MRI apparatus 10A compares the input-level information of a signal inputted into the RF power amplifier 43 during measurement in step ST31 with a threshold value. Accordingly, the degree of coupling of the directional coupler 44A configured to attenuate the RF signal transferred to the transmission coil 26 is controlled (step ST32').

In step ST4, the MRI apparatus 10A compares the input-level information predicted in step ST41 with the threshold value so as to control the degree of coupling of the directional coupler 44A configured to attenuate the RF signal transferred to the transmission coil 26 (step ST42').

According to the transmitter 27A of the MRI apparatus 10A according to the second embodiment, the intensity of an RF signal to be detected and AD-converted during pre-scan and main scan is controlled. As a result, even when an RF output is small, the RF output can accurately be measured with sufficient precision. Therefore, the MRI apparatus 10A according to the second embodiment is able to accurately calculate SAR with sufficient precision.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An apparatus for measuring radio frequency output for a magnetic resonance imaging apparatus, comprising:
   a plurality of directional couplers different in degree of coupling from each other, and configured to attenuate a radio frequency signal which is generated in a radio frequency signal generator and amplified in a radio frequency power amplifier;
   a comparator configured to compare input-level information of a signal inputted into the radio frequency power amplifier with a threshold value;
   a switcher configured to switch to any one of the plurality of the directional couplers based on a result of the comparison so as to output a radio frequency signal by the one directional coupler; and
   a converter configured to perform a digital conversion of the radio frequency signal from the one directional coupler so as to output a digital signal.

2. A magnetic resonance imaging apparatus, comprising:
   a static magnetic field magnet configured to generate a static magnetic field;
   a gradient coil configured to generate a gradient magnetic field where intensity of a magnetic field varies,
   a transmission coil which is a radio frequency coil configured to generate a radio frequency magnetic field;
   a radio frequency power amplifier configured to amplify a radio frequency signal generated in a radio frequency signal generator and to provide the amplified radio frequency signal to the transmission coil;
   a plurality of directional couplers different in degree of coupling from each other, and configured to attenuate the radio frequency signal amplified in the radio frequency power amplifier;
   a comparator configured to compare input-level information of the signal inputted into the radio frequency power amplifier with a threshold value;
   a switcher configured to switch to any one of the plurality of the directional couplers based on a result of the comparison so as to output a radio frequency signal by the one directional coupler;
   a converter configured to perform a digital conversion of the radio frequency signal from the one directional coupler so as to output a digital signal; and
   a calculator configured to calculate a specific absorbed fraction based on the radio frequency signal outputted from the converter.

3. The magnetic resonance imaging apparatus according to claim 2, wherein
   the input-level information is predicted based on a radio frequency level which is a radio frequency signal output in a case of an excitation pulse having a flip angle used as a reference.

4. The magnetic resonance imaging apparatus according to claim 3, wherein
   the radio frequency level is measured in each object and in each imaging region.

5. The magnetic resonance imaging apparatus according to claim 3, wherein
   the input-level information is set for each radio frequency pulse included in a pulse sequence based on the radio frequency level.

6. The magnetic resonance imaging apparatus according to claim 5, wherein
   the radio frequency pulse included in the pulse sequence includes a pre-pulse and an excitation pulse.

* * * * *